United States Patent
Katayose

(10) Patent No.: US 9,504,854 B2
(45) Date of Patent: Nov. 29, 2016

(54) ROTATING GANTRY AND PARTICLE BEAM THERAPY SYSTEM

(75) Inventor: Tadashi Katayose, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/365,946

(22) PCT Filed: Mar. 29, 2012

(86) PCT No.: PCT/JP2012/058365
§ 371 (c)(1),
(2), (4) Date: Jun. 16, 2014

(87) PCT Pub. No.: WO2013/145211
PCT Pub. Date: Oct. 3, 2013

(65) Prior Publication Data
US 2014/0364677 A1    Dec. 11, 2014

(51) Int. Cl.
*A61N 5/10* (2006.01)
*G21F 3/00* (2006.01)
*G21K 1/02* (2006.01)
*G21K 1/093* (2006.01)
(Continued)

(52) U.S. Cl.
CPC ............... *A61N 5/1081* (2013.01); *G21F 3/00* (2013.01); *G21F 7/00* (2013.01); *G21K 1/02* (2013.01); *G21K 1/093* (2013.01); *G21K 1/10* (2013.01); *A61N 2005/109* (2013.01); *A61N 2005/1087* (2013.01); *A61N 2005/1094* (2013.01)

(58) Field of Classification Search
USPC ............................................ 250/492.3, 515.1
See application file for complete search history.

(56) References Cited

U.S. PATENT DOCUMENTS

| | | |
|---|---|---|
| 5,577,094 A | 11/1996 | Fudamoto |
| 6,683,318 B1 | 1/2004 | Haberer et al. |
| 8,139,714 B1 | 3/2012 | Sahadevan |

(Continued)

FOREIGN PATENT DOCUMENTS

| | | |
|---|---|---|
| CN | 2432949 Y | 6/2001 |
| CN | 1586669 A | 3/2005 |

(Continued)

OTHER PUBLICATIONS

Taiwanese Office Action issued by the Taiwan Intellectual Property Office on Sep. 1, 2015 in corresponding Taiwan Application No. 101134880 (12 pages).

(Continued)

*Primary Examiner* — Kiet T Nguyen
(74) *Attorney, Agent, or Firm* — Buchanan Ingersoll & Rooney PC

(57) ABSTRACT

A rotating gantry is characterized in that a shielding material for attenuating a leakage dose of a secondary radiation generated by collision of a charged particle beam with an irradiation subject is provided at a position that is situated at the side opposed to a particle beam irradiation apparatus with respect to the irradiation subject and through which a beam axis of the charged particle beam passes, and wherein the shielding material is disposed in such a way that when the irradiation subject does not exist in the rotating gantry, a beam axis portion thereof that intersects the beam axis of the charged particle beam, is attachable and detachable, or can move in a sliding manner and in the rotation-axle direction of the rotating gantry.

7 Claims, 14 Drawing Sheets

(51) Int. Cl.
*G21K 1/10* (2006.01)
*G21F 7/00* (2006.01)

(56) References Cited

U.S. PATENT DOCUMENTS

| | | | |
|---|---|---|---|
| 2009/0194713 A1 | 8/2009 | Stichelbaut et al. | |
| 2011/0101246 A1 | 5/2011 | Yajima et al. | |
| 2012/0033790 A1* | 2/2012 | Wilfley | A61N 5/1049 378/65 |
| 2012/0150018 A1 | 6/2012 | Yamaya et al. | |

FOREIGN PATENT DOCUMENTS

| | | |
|---|---|---|
| CN | 101810910 A | 8/2010 |
| JP | 39-13090 Y1 | 5/1964 |
| JP | 51-45599 | 4/1976 |
| JP | 07-039592 A | 2/1995 |
| JP | 7-227432 A | 8/1995 |
| JP | 08-010343 A | 1/1996 |
| JP | 2002-525135 A | 8/2002 |
| JP | 2009-539088 A | 11/2009 |
| JP | 2011-092424 A | 5/2011 |
| JP | 2012-055701 A | 3/2012 |
| TW | 201034530 A | 9/2010 |
| WO | WO 2010/109586 A1 | 9/2010 |

OTHER PUBLICATIONS

Taiwanese Office Action issued by the Taiwan Intellectual Property Office on Dec. 28, 2015 in corresponding Taiwan Application No. 101134880 (7 pages).
Japanese Office Action dated Feb. 10, 2015 issued in corresponding Japanese Patent Appln. No. 2014-507177, with English translation (9 pages).
Chinese Office Action issued by the Chinese Intellectual Property Office on Jan. 26, 2016 in corresponding Chinese Application No. 201280072085 and English language translation (10 pages).
International Search Report (PCT/ISA/210) mailed on Jul. 3, 2012, by the Japanese Patent Office as the International Searching Authority for International Application No. PCT/JP2012/058365.
Taiwanese Office Action issued by the Intellectual Property Office of Taiwan on May 11, 2016 in corresponding Taiwanese Application No. 104139906 and English language translation (7 pages).

* cited by examiner

ROTATING GANTRY AND PARTICLE BEAM THERAPY SYSTEM

TECHNICAL FIELD

The present invention relates to a particle beam therapy system that is utilized in the medical field.

BACKGROUND ART

In general, a particle beam therapy system is provided with a beam generation apparatus that generates a charged particle beam, an accelerator that is connected with the beam generation apparatus and accelerates a generated charged particle beam, a beam transport system that transports a charged particle beam that is accelerated by the accelerator so as to gain predetermined energy and then emitted, and a particle beam irradiation apparatus, disposed at the downstream side of the beam transport system, for irradiating a charged particle beam onto an irradiation subject. In order to irradiate a charged particle beam onto an irradiation subject at an arbitrary angle, a particle beam irradiation apparatus is disposed in a three-dimension-irradiation rotating gantry.

Patent Document 1 discloses a particle beam irradiation apparatus installed in a building covered with a concrete radiation shielding material. The particle beam irradiation apparatus disclosed in Patent Document 1 is a rotating gantry; this rotating gantry is provided with a treatment table on which a patient lies, an irradiation unit that irradiates a proton beam onto a patient, and an introduction line that introduces a proton beam, which is guided by a guide line, into the irradiation unit. In this rotating gantry, in order to ensure the balance between the introduction line and a stand, counter weights are arranged at the positions that are on the outer circumferential surface of a cylinder portion and face each other with respect to the rotation axis.

PRIOR ART REFERENCE

Patent Document

[Patent Document 1] Japanese Patent Application Laid-Open No. 2011-92424 (Paragraphs 0015 to 0030, FIGS. 1 and 3)

DISCLOSURE OF THE INVENTION

Problems to be Solved by the Invention

Because utilizing a high-energy charged particle beam, a particle beam therapy system needs to be surrounded with a shielding material such as a concrete radiation shielding material. In a treatment room where a rotating gantry is disposed, due to the rotation of the rotating gantry, a charged particle beam such as a proton beam is irradiated onto an irradiation subject such as a patient or a phantom at an arbitrary angle; thus, in order to prevent as much as possible a high-penetrability radiation such as a neutron beam or a gamma ray, which is produced by the collision of the charged particle beam with the irradiation subject, from leaking toward the outside of the room, the treatment room and its periphery need to be surrounded with a several-meter-thickness shielding material such as concrete that is concurrently utilized as a building.

In the rotating gantry disclosed in Patent Document 1, no contrivance is taken into consideration with which a high-penetrability radiation such as a neutron beam or a gamma ray, which is produced by the collision of the charged particle beam with the irradiation subject, is shielded. In the rotating gantry disclosed in Patent Document 1, when the irradiation direction of a charged particle beam changes in accordance with the rotation angle of the rotating gantry, the direction of a high-penetrability radiation radiated from the irradiation subject changes; therefore, the whole irradiation chamber needs to be surrounded with thick concrete and hence it is difficult to downsize the building that contains the particle beam therapy system.

The present invention has been implemented in order to solve the foregoing problems; the objective thereof is to prevent a radiation from leaking out of the rotating gantry, by providing in the rotating gantry a shielding material that reduces the leakage of a high-penetrability radiation (referred to as a secondary radiation, hereinafter) such as a neutron beam or a gamma ray.

Means for Solving the Problem(s)

A rotating gantry according to the present invention is characterized in that a shielding material for attenuating the leakage dose of a secondary radiation generated by collision of a charged particle beam with an irradiation subject is provided at a position that is situated at the side opposed to the particle beam irradiation apparatus with respect to the irradiation subject and through which a beam axis of the charged particle beam passes, and wherein the shielding material is disposed in such a way that when the irradiation subject does not exist in the rotating gantry, a beam axis portion thereof that intersects the beam axis of the charged particle beam, is attachable and detachable, or can move in a sliding manner and in the rotation-axle direction of the rotating gantry.

Advantage of the Invention

In a rotating gantry according to the present invention, a shielding material for attenuating the leakage dose of a secondary radiation is provided at the downstream side of an irradiation subject; therefore, a second radiation, especially generated forward in the beam axis with a high probability, can be prevented from leaking out of the gantry.

BEST MODE FOR CARRYING OUT THE INVENTION

Embodiment 1

Figure 1:
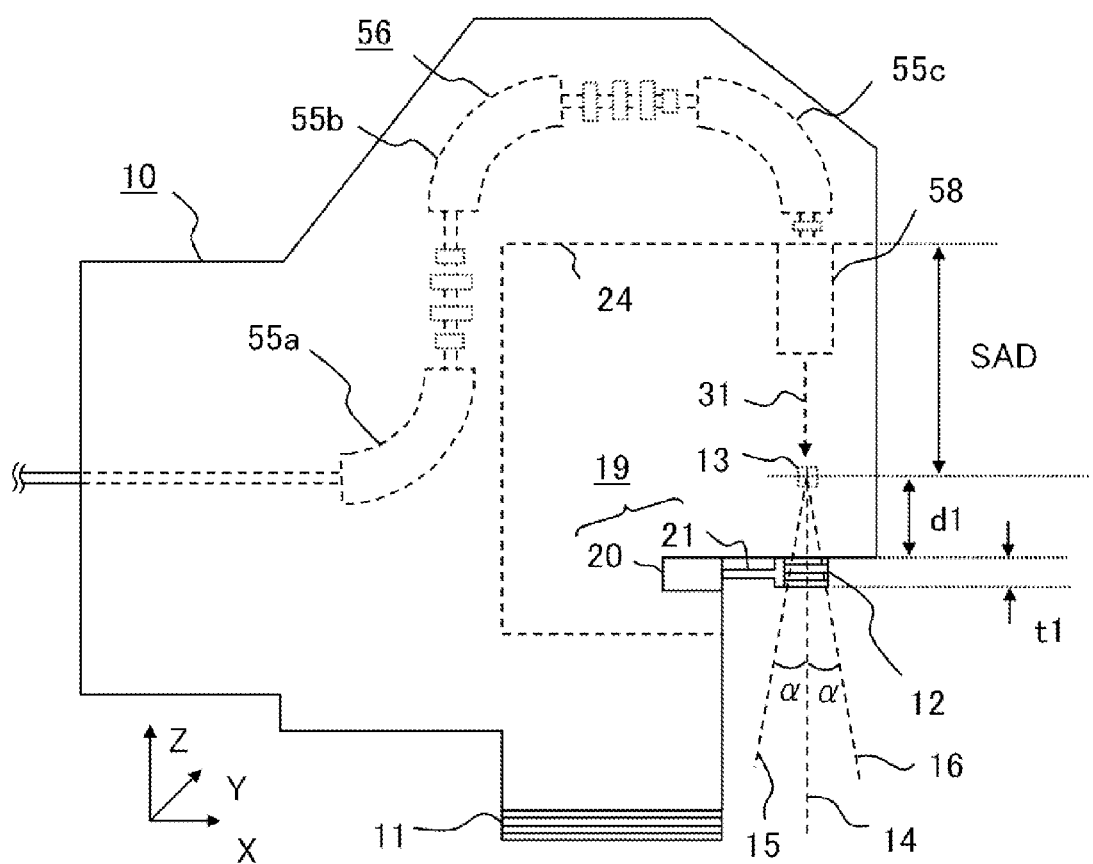
FIG. 1 is a diagram representing the configuration of a rotating gantry according to Embodiment 1 of the present invention.
Figure 2:
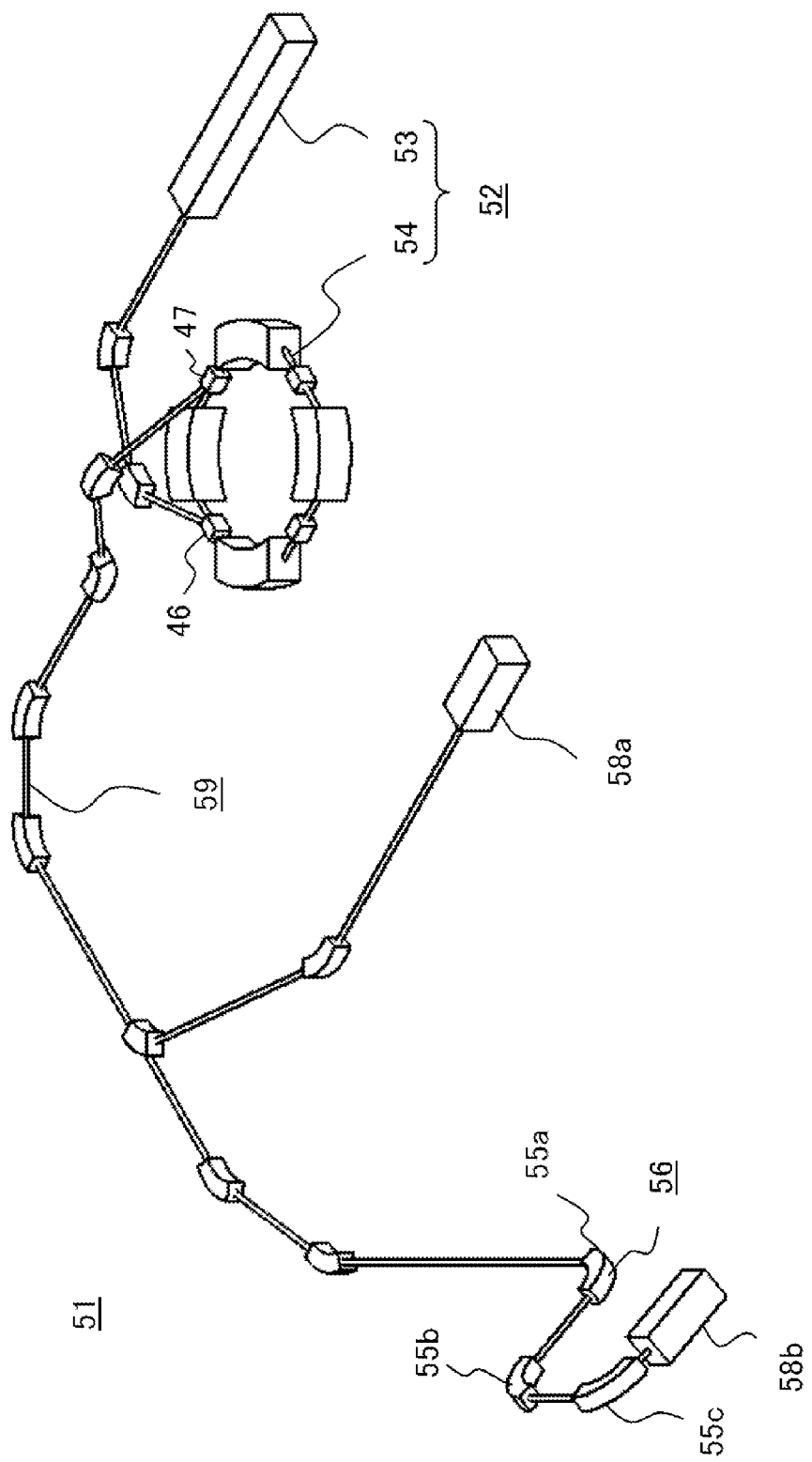
FIG. 2 is a schematic configuration diagram representing a particle beam therapy system according to Embodiment 1 of the present invention.
Figure 3:
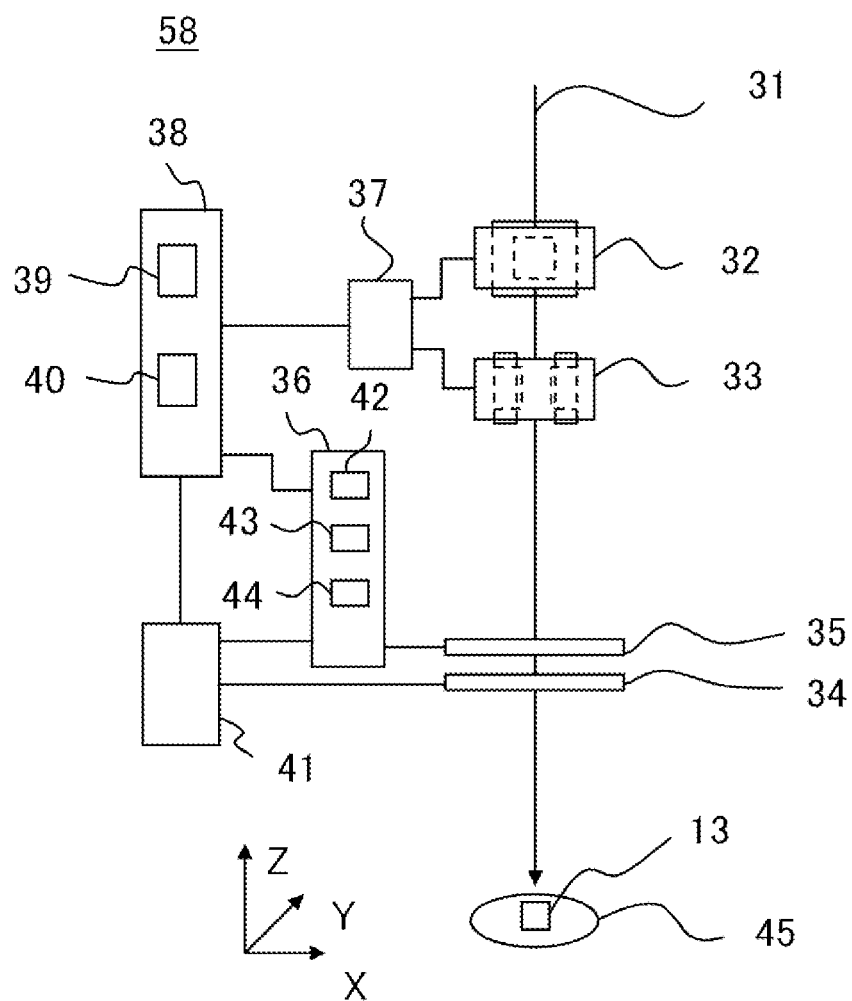
FIG. 3 is a diagram representing the configuration of the particle beam irradiation apparatus in FIG. 2.

FIG. 1 is a diagram representing the configuration of a rotating gantry according to Embodiment 1 of the present invention. FIG. 2 is a schematic configuration diagram representing a particle beam therapy system according to Embodiment 1 of the present invention; FIG. 3 is a diagram illustrating the configuration of a particle beam irradiation apparatus according to Embodiment 1 of the present invention. In FIG. 2, a particle beam therapy system 51 includes a beam generation apparatus 52, a beam transport system 59, and particle beam irradiation apparatuses 58a and 58b. The beam generation apparatus 52 includes an ion source (unillustrated), a prestage accelerator 53, and a synchrotron 54. The particle beam irradiation apparatus 58b is provided in a rotating gantry (refer to FIG. 1). The particle beam irradiation apparatus 58a is provided in a treatment room where no rotating gantry is installed. The function of the beam transport system 59 is to achieve communication between the synchrotron 54 and the particle beam irradiation apparatuses 58a and 58b. Part of the beam transport system 59 is provided in the rotating gantry (refer to FIG. 1), and that part includes a plurality of deflection electromagnets 55a, 55b, and 55c. Part of the beam transport system 59 provided in the rotating gantry is a rotating gantry mounting portion 56.

A charged particle beam, which is a particle beam such as a proton beam generated in the ion source, is accelerated by the prestage accelerator 53 and injected into the synchrotron 54 through an injector 46. The particle beam is accelerated to gain predetermined energy. The charged particle beam launched from a launching apparatus 47 of the synchrotron 54 is transported to the particle beam irradiation apparatuses 58a and 58b by way of the beam transport system 59. The particle beam irradiation apparatuses 58a and 58b each irradiate the charged particle beam onto an irradiation subject 13 (refer to FIG. 3) of a patient 45. As the reference numeral of the particle beam irradiation apparatus, "58" is collectively utilized; however, in the case where the apparatuses are separately explained, "58a" and "58b" are utilized.

A charged particle beam 31 generated in the beam generation apparatus 52 and accelerated to gain predetermined energy is led to the particle beam irradiation apparatus 58 by way of the beam transport system 59. In FIG. 3, the particle beam irradiation apparatus 58 is provided with X-direction and Y-direction scanning electromagnets 32 and 33 that scan the charged particle beam 31 in the X direction and the Y direction, respectively, which are directions perpendicular to the charged particle beam 31; a position monitor 34; a dose monitor 35; a dose data converter 36; a beam data processing apparatus 41; a scanning electromagnet power source 37; and an irradiation management apparatus 38 that controls the particle beam irradiation apparatus 58. The irradiation management apparatus 38 is provided with an irradiation control computer 39 and an irradiation control apparatus 40. The dose data converter 36 is provided with a trigger generation unit 42, a spot counter 43, and an inter-spot counter 44. The traveling direction of the charged particle beam 31 is −Z direction.

The X-direction and Y-direction scanning electromagnets 32 and 33 scan the charged particle beam 31 in the X direction and the Y direction, respectively. The position monitor 34 detects beam information for calculating the passing position (gravity center position) through which the charged particle beam 31 that has been scanned by the X-direction scanning electromagnet 32 and the Y-direction scanning electromagnet 33 passes and the size of the charged particle beam 31. The beam data processing device 41 calculates the passing position (gravity center position) and the size of the charged particle beam 31, based on beam information including a plurality of analogue signals (beam information items) detected by the position monitor 34. Moreover, the beam data processing device 41 generates an abnormality detection signal indicating a positional abnormality or a dimensional abnormality of the charged particle beam 31 and outputs the abnormality detection signal to the irradiation management apparatus 38.

The dose monitor 35 detects the dose of the charged particle beam 31. The irradiation management apparatus 38 controls the irradiation position of the charged particle beam 31 on the irradiation subject 13, based on treatment plan data created by an unillustrated treatment planning apparatus; when the dose measured by the dose monitor 35 and converted into digital data by the dose data converter 36 reaches a desired dose, the charged particle beam 31 is stopped. The scanning electromagnet power source 37 changes setting currents for the X-direction scanning electromagnet 32 and the Y-direction scanning electromagnet 33, based on control inputs (commands), which are outputted from the irradiation management apparatus 38, to the X-direction scanning electromagnet 32 and the Y-direction scanning electromagnet 33.

In this Description, the scanning irradiation method for the particle beam irradiation apparatus 58 will be explained assuming that it is the raster-scanning irradiation method in which when the irradiation position of the charge particle beam is changed, the charged particle beam 31 is not stopped, i.e., it is a method in which as is the case with the spot scanning irradiation method, the beam irradiation position travels through spot positions one after another. The spot counter 43 measures the irradiation dose for a time during which the beam irradiation position of the charged particle beam 31 is stopped. The inter-spot counter 44 measures the irradiation dose for a time during which the beam irradiation position of the charged particle beam 31 moves. The trigger generation unit generates a dose completion signal when the dose of the charged particle beam 31 at the beam irradiation position reaches the desired dose.

In FIG. 1, a rotating gantry 10 is provided with a gantry inner chamber 24, a counter weight 11, a shielding material 12, and a shielding material moving apparatus 19. The rotating gantry mounted portion 56 of the beam transport system 59 and the particle beam irradiation apparatus 58 are provided in the rotating gantry 10. In order to ensure the balance between the rotating gantry mounting portion 56 provided in the rotating gantry 10 and the counter weight 11, the counter weight 11 is provided at the side opposite to the rotating gantry mounting portion 56. The shielding material 12 attenuates a high-penetrability radiation such as a neutron beam or a gamma ray, which is produced by the collision of the charged particle beam with the irradiation subject 13. The shielding material moving apparatus 19 includes a driving rod 21 with which the shielding material 12 is connected and a driving apparatus 20 that moves the driving rod 21. The shielding material 12 is formed of, for example, two or more iron plates that are stacked on top of the other. Even when the irradiation subject 13 is water as a phantom, its collision with the charged particle beam 31 produces a high-penetrability radiation (secondary radiation) such as a neutron beam or a gamma ray. Respective quadrupole electromagnets or the likes for making the charged particle beam converge or diverge may be arranged between the deflection electromagnets 55a and 55b or 55b and 55c and/or between the deflection electromagnet 55c and the particle beam irradiation apparatus 58.

In FIG. 1, a distance SAD (Source Axis Distance) is a distance between a particle-beam enlargement starting position and the center of the irradiation subject 13 of the patient 45; a shielding material distance d1 is a distance between the shielding material 12 and the center of the irradiation subject 13. A shielding material thickness t1 is a thickness of the shielding material 12 in the traveling direction of the charged particle beam 31. A secondary radiation produced by the collision of the charged particle beam 31 with the irradiation subject 13 is strongly radiated, especially in the range within a predetermined angle α from the beam center line 14. A radiation outer circumference line 15 is a traveling line at a time when a secondary radiation travels at the angle α leftward on the plane of the paper (in the −X direction) in FIG. 1, i.e., an outer circumference line at a time when a secondary radiation travels while spreading in the range within the angle α. A radiation outer circumference line 16 is a traveling line at a time when a secondary radiation travels at the angle α rightward on the plane of the paper (in the X direction) in FIG. 1, i.e., an outer circumference line at a time when a secondary radiation travels while spreading in the range within the angle α. Because the shielding material 12 attenuates the leakage dose of a secondary radiation, which provides a large effect to the thickness of the shielding wall of the building, the present invention will be examined in terms of the traveling direction of a secondary radiation. For example, in the case where the angle α is 10°, the intensity and the energy of a produced secondary radiation is especially large. The shielding material 12 is provided in the rotating gantry 10 in such a way that the angle α covers the range within 10°.

FIG. 1 represents a case where the charged particle beam 31 is scanned by neither the X-direction scanning electromagnet 32 nor the Y-direction scanning electromagnet 33. There will be considered an X-direction width W1 under the condition that a secondary radiation radiated in the range within the angle α passes through the shielding material 12. The width W1 can be given by the equation (1).

$$W1 = 2 \times (d1 + t1) \times \tan\alpha \qquad (1)$$

Assuming that the shielding material distance d1, the shielding material thickness t1, and the angle α are 1000 mm, 400 mm, and 10°, respectively, the width W1 is 494 mm according to the equation (1). Accordingly, in the case where the shielding material distance d1, the shielding material thickness t1, and the angle α are 1000 mm, 400 mm, and 10°, respectively, the width of the shielding material 12 in a direction perpendicular to the traveling direction of the charged particle beam 31 needs to be 494 mm or longer.

Figure 4:
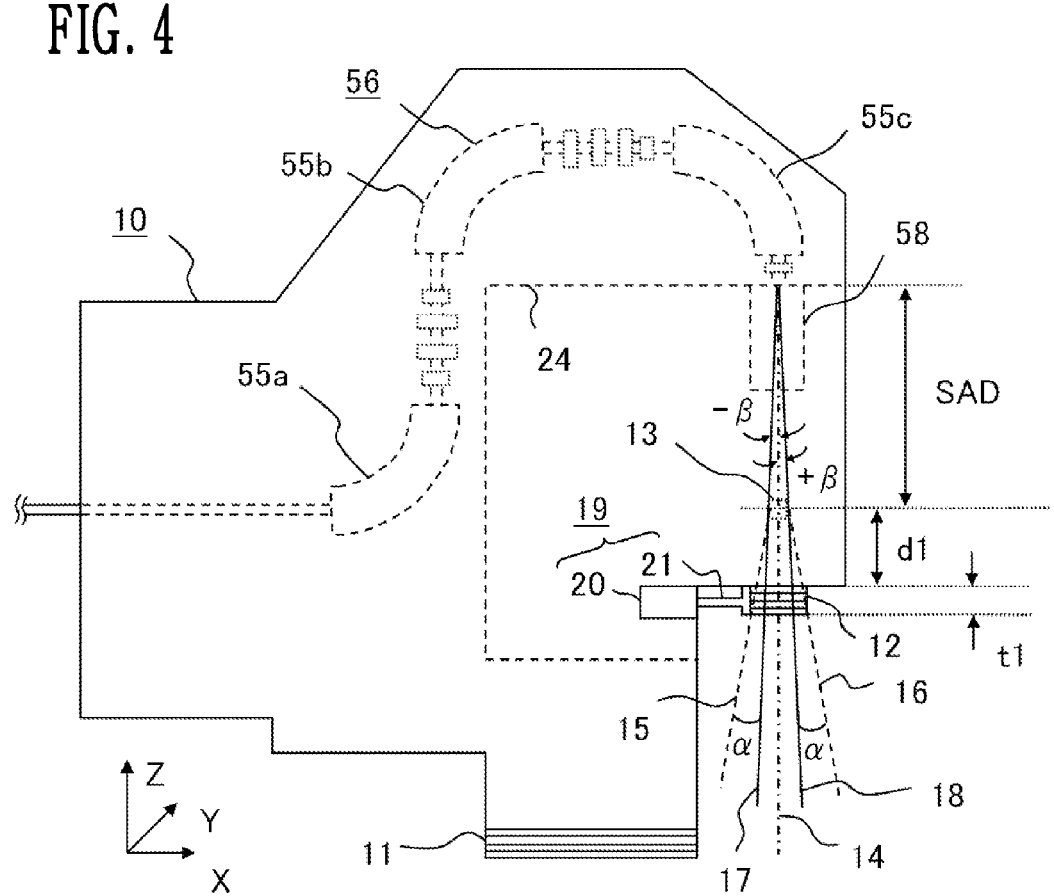
FIG. 4 is a diagram for explaining the width of a shielding material according to Embodiment 1 of the present invention.

In the case of a particle beam therapy that is actually implemented, the charged particle beam 31 is scanned by the X-direction scanning electromagnet 32 and the Y-direction scanning electromagnet 33, and hence the irradiation field is enlarged transversely. The width of the shielding material 12, required when the irradiation field is transversely enlarged, will be explained with reference to FIG. 4. FIG. 4 is a diagram for explaining the width of a shielding material according to Embodiment 1 of the present invention. A beam outer circumference line 17 is a −X-direction outmost circumference beam path at a time when the charged particle beam 31 is scanned at a scanning angle −β; a beam outer circumference line 18 is an X-direction outmost circumference beam path at a time when the charged particle beam 31 is scanned at a scanning angle +β. With regard to the scanning angle β, the counterclockwise direction with respect to the beam center line 14 will be referred to the positive direction (+ direction); the clockwise direction with respect to the beam center line 14 will be referred to the negative direction (− direction). Assuming that the enlarged width (scanning width) of the charged particle beam 31 at the irradiation subject 13 is ws, an X-direction width W2 under the condition that a secondary radiation radiated in the range within the angle α passes through the shielding material 12 can be given by the equation (2).

$$W2 = ws + 2 \times (d1 + t1) \times \tan(\alpha + \beta) \qquad (2)$$

Assuming that the distance SAD, the shielding material distance d1, the shielding material thickness t1, the enlarged width ws, and the angle α are 3000 mm, 1000 mm, 400 mm, 200 mm, and 10°, respectively, the width W2 is 791 mm according to the equation (2). In this case, the width of the shielding material in a direction perpendicular to the traveling direction of the charged particle beam 31 needs to be 791 mm or longer. The width of the shielding material 12 is determined by considering the scanning range of the charged particle beam 31, i.e., the enlarged width (scanning width) ws of the charged particle beam 31 at the irradiation subject 13 and the angle α of a secondary radiation. In the rotating gantry 10 according to Embodiment 1 is provided with the shielding material 12 having a width within the angle α, through which a secondary radiation passes, by considering the scanning range of the charged particle beam 31 and the angle α of the secondary radiation; therefore, the leakage dose of the secondary radiation within the angle α can be attenuated.

Figure 5:
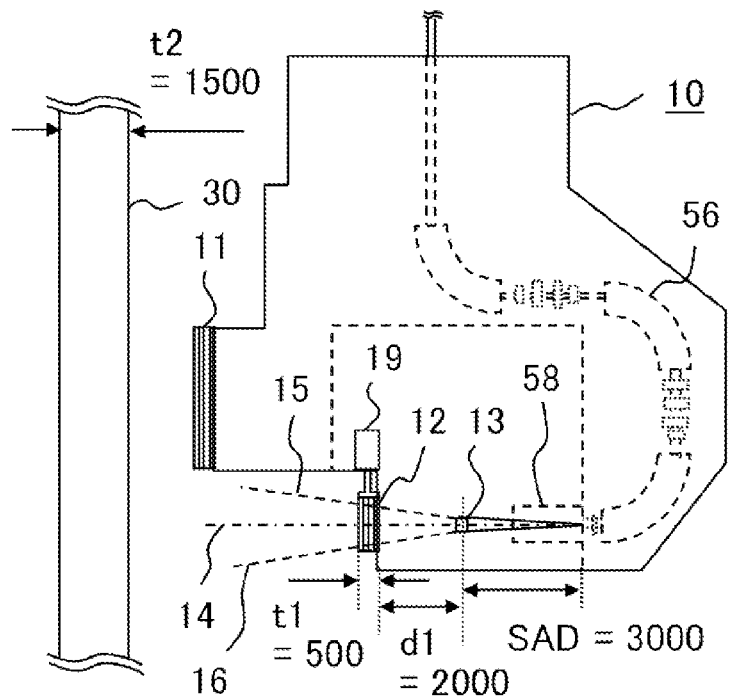
FIG. 5 is a diagram for explaining the effect of a shielding material according to Embodiment 1 of the present invention.
Figure 6:
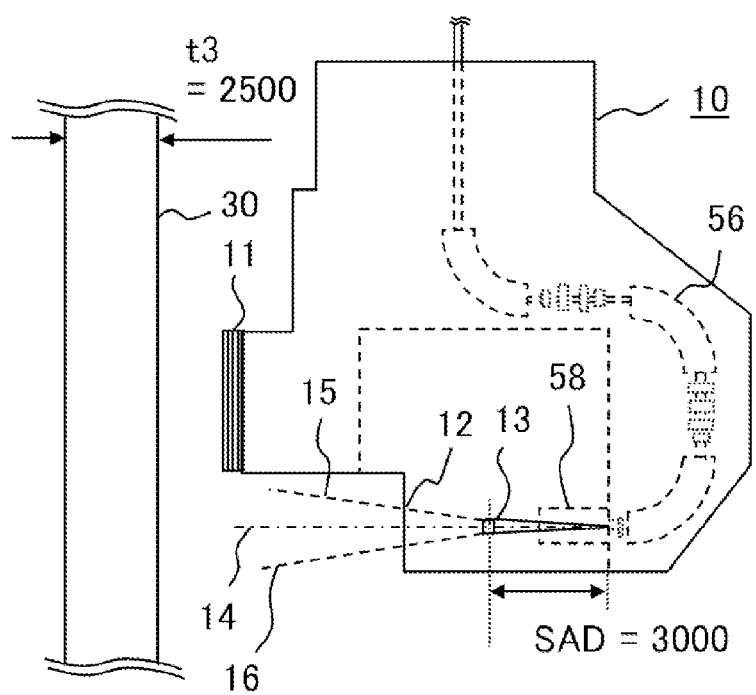
FIG. 6 is a diagram for explaining the thickness of a wall at a time when no shielding material is provided.

Next, the effect that can be obtained by utilizing the shielding material 12 will be explained. When the secondary radiation passes through the shielding material 12, the leakage dose thereof is attenuated; thus, the thicknesses of the wall and the floor of the treatment room where the rotating gantry 10 according to Embodiment 1 is installed can be reduced in comparison with a conventional rotating gantry. FIG. 5 is a diagram for explaining the effect of the shielding material according to Embodiment 1 of the present invention; FIG. 6 is a diagram for explaining the thickness of the wall at a time when no shielding material is provided. For example, there will be considered a case where the charged particle of the charged particle beam 31 to be irradiated onto the irradiation subject is a carbocation and the energy of the charged particle is 400 MeV/n (400 MeV per nucleon). In each of FIGS. 5 and 6, the distance SAD is 3000 mm. In FIG. 5, the shielding material distance d1 is 2000 mm, and the thickness t1 of an iron shielding material is 500 mm. When a carbocation having energy of 400 MeV/n collides with the irradiation subject 13, the iron thickness required for halving the effective dose of a neutron that is produced in the traveling direction of the carbocation is approximately the half of the thickness of concrete. Therefore, the iron shielding material having a thickness t1 of 500 mm corresponds to concrete having a thickness of 1 m.

In order to obtain the same shielding effect as that of a concrete treatment room wall 30, having a thickness t3 of 2500 mm, that is illustrated in FIG. 6, an iron shielding material, having a thickness t1 of 500 mm, that is illustrated in FIG. 5 is installed in the rotating gantry, so that the thickness t2 of the concrete treatment room wall can be set to 1500 mm. In other words, when an iron shielding material having a thickness t1 of 500 mm is installed in the rotating gantry, a conventional concrete treatment room wall having a thickness t3 can be replaced by a concrete treatment room wall having a thickness t2, which is 1 m thinner than the thickness t3. This means that the wall thickness, which has needed to be t3 so far, can be reduced to t2. This is because the secondary-radiation attenuation capability corresponding to the difference $\Delta t$ (=t3−t2) is exerted by the shielding material 12.

In the rotating gantry 10 according to Embodiment 1, the shielding material 12 is provided at the side opposed to the particle beam irradiation apparatus 58 with respect to the irradiation subject 13, i.e., at the downstream side of the irradiation subject 13; therefore, the leakage dose of a secondary radiation passing through the shielding material 12 can be attenuated and hence the secondary radiation can be prevented from leaking from the rotating gantry 10. Because the secondary radiation is attenuated by the shielding material 12, the thicknesses of the wall and the floor of the treatment room where the rotating gantry 10 is installed can be reduced in comparison with a conventional rotating gantry; thus, the treatment room can be downsized. Because the treatment room can be downsized, the building for containing the particle beam therapy system 51 can be downsized.

Figure 7:
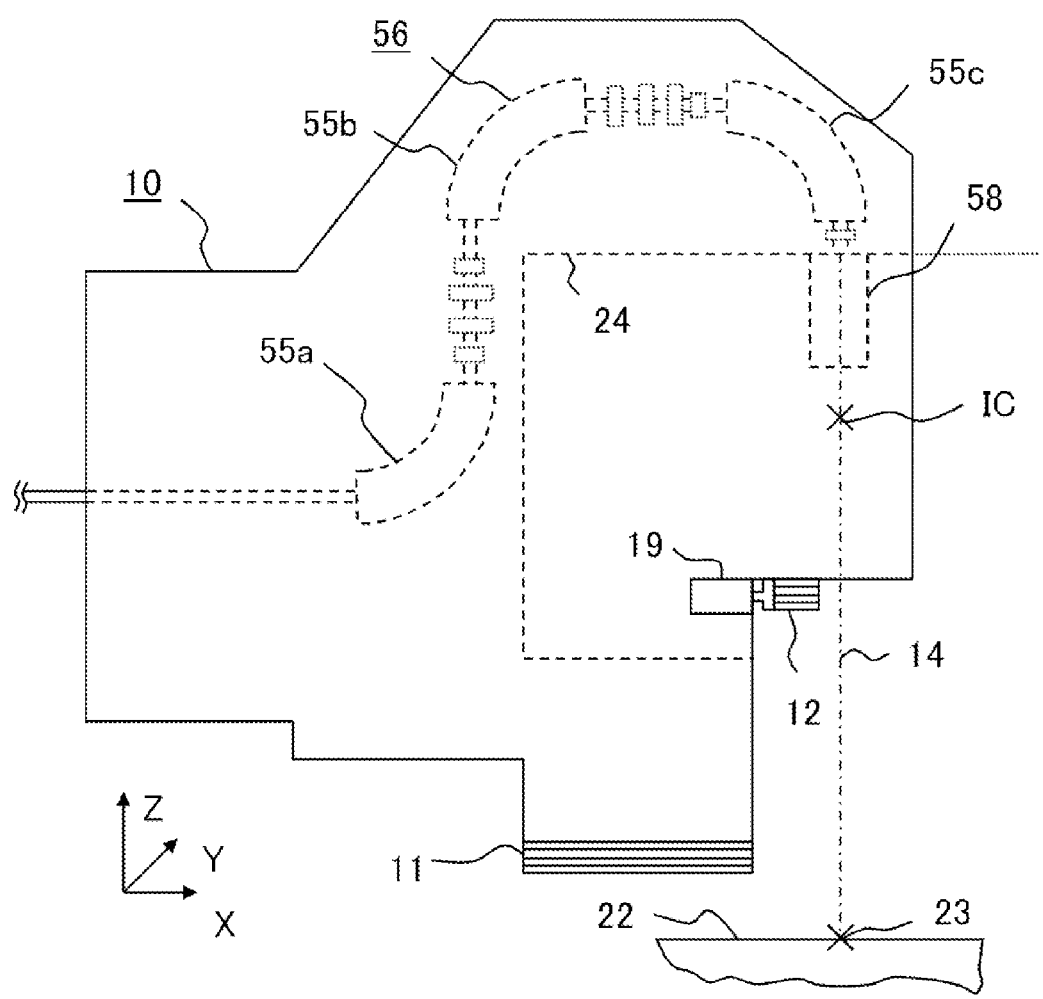
FIG. 7 is a diagram representing the rotating gantry at a time when the shielding material is moved.

It is periodically ascertained whether or not the positional relationship between the rotating gantry 10 and the building is within a tolerance range; when the misalignment is large, the position thereof is adjusted. When the positional relationship between the rotating gantry 10 and the building is ascertained or the position adjustment is implemented, the shielding material 12 is moved. FIG. 7 is a diagram representing the rotating gantry at a time when the shielding material is moved. In FIG. 7, an isocenter IC is a point at which beam center lines 14 intersect one another when the rotating gantry 10 rotates. When the positional relationship between the rotating gantry 10 and the building is ascertained or the position adjustment is implemented, the isocenter IC and a floor reference mark 23 on a building floor 22 are optically ascertained. In this situation, because the shielding material prevents the optical ascertainment from being implemented, the driving apparatus 20 in the shielding material moving apparatus 19 is operated so as to move the shielding material 12 in a sliding manner. By preventing the shielding material 12 from obstructing the beam center line 14, the isocenter IC and the floor reference mark 23 on the building floor 22 can optically be ascertained.

In the rotating gantry 10 according to Embodiment 1, the shielding material 12 for attenuating the leakage dose of a secondary radiation produced by the collision of the charged particle beam 31 with the irradiation subject 13 is provided at the side opposed to the particle beam irradiation apparatus 58 with respect to the irradiation subject 13; therefore, the secondary radiation can be prevented from leaking from the rotating gantry 10.

The particle beam therapy system 51 according to Embodiment is provided with the beam generation apparatus 52 that generates the charged particle beam 31 and accelerates the charged particle beam 31 by means of an accelerator (the synchrotron 54), the beam transport system 59 that transports the charged particle beam 31 accelerated by the accelerator (synchrotron 54), the particle beam irradiation apparatus 58 that irradiates the charged particle beam 31 transported by the beam transport system 59 onto the irradiation subject 13, and the rotating gantry 10 that is equipped with the particle beam irradiation apparatus 58 and can rotate around the isocenter. Because in the rotating gantry 10, the shielding material 12 for attenuating the leakage dose of a secondary radiation produced by the collision of the charged particle beam 31 with the irradiation subject 13 is provided at the side opposed to the particle beam irradiation apparatus 58 with respect to the irradiation subject 13, the secondary radiation can be prevented from leaking from the rotating gantry 10; therefore, the thicknesses of the wall and the floor of the treatment room where the rotating gantry 10 is installed can be reduced in comparison with a conventional rotating gantry, and hence the treatment room can be downsized. Because the treatment room can be downsized, the building for containing the particle beam therapy system 51 can be downsized.

Embodiment 2

Figure 8:
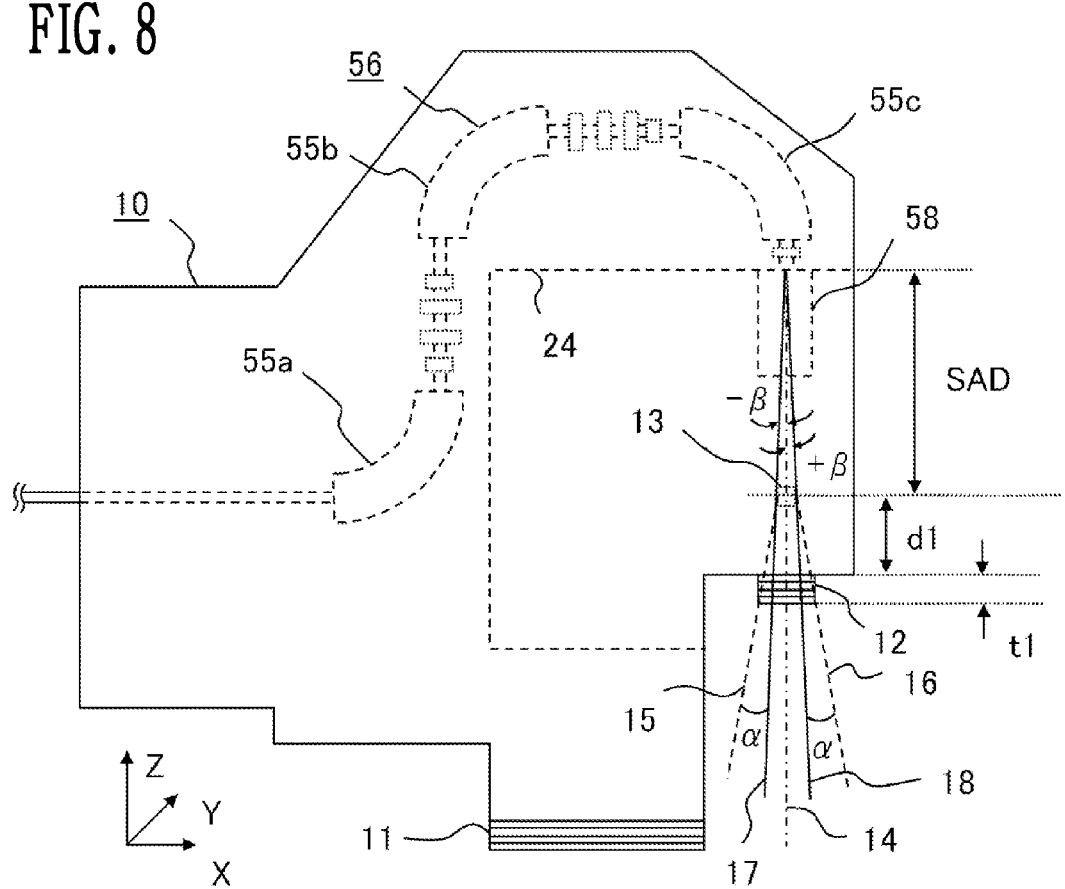
FIG. 8 is a diagram representing the configuration of a rotating gantry according to Embodiment 2 of the present invention.
Figure 9:
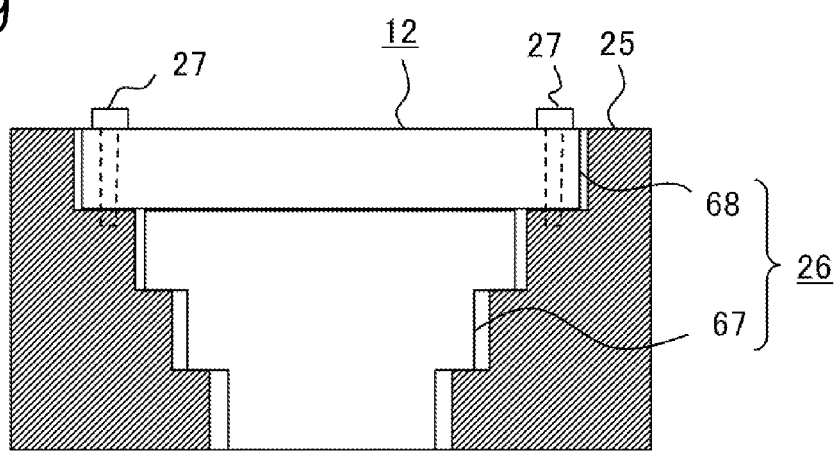
FIG. 9 is a diagram representing the shielding material in FIG. 8.

FIG. 8 is a diagram representing the configuration of a rotating gantry according to Embodiment 2 of the present invention; FIG. 9 is a diagram representing a shielding material according to Embodiment 2. The rotating gantry 10 according to Embodiment 2 differs from the rotating gantry 10 according to Embodiment 1 in that the shielding material moving apparatus 19 is not included therein and in that the shielding material 12 is configured with a foundation portion 25 and a detachable portion including a first detachable portion 67 and a second detachable portion 68. In FIG. 9, the foundation portion 25 is represented by a cross section so that the detachable portion 26 is exposed.

In the shielding material 12 according to Embodiment 2, the foundation portion 25 is connected with the second detachable portion 68 in the detachable portion 26, by means of a bolt 27. FIG. 9 shows an example in which the foundation portion 25 and the detachable portion 26 each have a 4-iron-plate laminated structure and stepped engagement portions. The first detachable portion 67 includes three iron sheets, and the second detachable portion 68 includes one iron sheet. After the first detachable portion 67 is inserted into the foundation portion 25, the second detachable portion 68 is mounted in such a way as to cover the first detachable portion 67. FIG. 9 shows an example in which the engagement portion where the detachable portion 26, which is attachable and detachable, engages with the foundation portion 25 includes a portion that is parallel to the beam axis (the axis that passes through the beam center line 14) of the charged particle beam 31 and a portion that is perpendicular to the beam axis. When the positional relationship between the rotating gantry 10 and the building is ascertained or the position adjustment is implemented, the detachable portion 26 is detached, so that the isocenter IC and a floor reference mark 23 on the building floor 22 can optically be ascertained.

Figure 10:
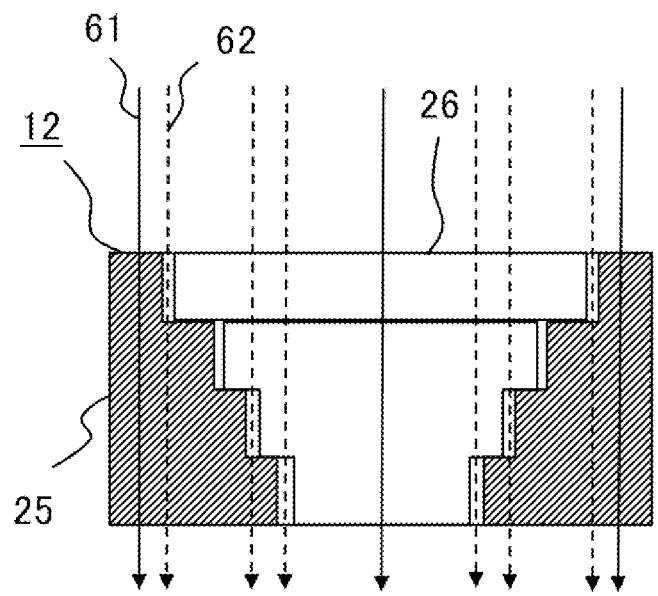
FIG. 10 is a diagram representing the attenuation effect of the shielding material in FIG. 8.
Figure 11:
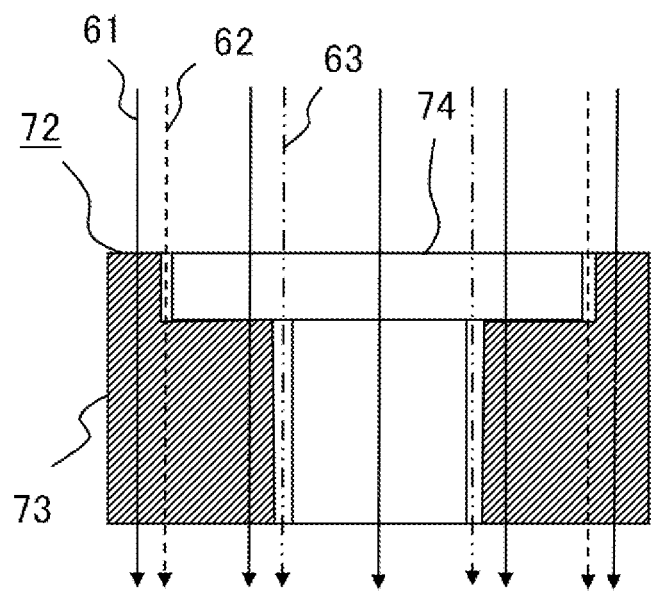
FIG. 11 is a diagram representing a comparative example.

In terms of attenuation of the leakage dose of a secondary radiation, it is significant that as represented in FIG. 9, there is utilized a configuration in which the respective shapes of the foundation portion 25 and the detachable portion 26 of the shielding material 12 differ from each other in the beam axis direction, i.e., no engagement portion that accounts for the half or more of the shielding material 12 exists in the axis direction. The significance will be explained with reference to FIGS. 10 and 11. FIG. 10 represents the attenuation effect of the shielding material; FIG. 11 represents a comparative example. A shielding material 72 of the comparative example represented in FIG. 11 includes a foundation portion 73 and a detachable portion 74. Two or more arrows indicate that secondary radiations such as neutron beams travel straightforward with a certain width. In the shielding material 12 according to Embodiment 2 represented in FIG. 10, a neutron passing therethrough as indicated by an arrow 61 penetrates four iron plates; a neutron passing therethrough as indicated by an arrow 62 penetrates three iron plates. Accordingly, the shielding material 12 has a secondary-radiation attenuation effect corresponding to that of at least three iron plates.

In contrast, in the shielding material 72 represented in FIG. 11, a neutron passing therethrough as indicated by the arrow 61 penetrates four iron plates, and a neutron passing therethrough as indicated by the arrow 62 penetrates three iron plates; however, a neutron passing therethrough as indicated by an arrow 63 penetrates one iron plate. In comparison with the shielding material 12, the shielding material 72 of the comparative example has a small effect of attenuating the leakage dose of a secondary radiation.

Therefore, when in the shielding material 12 according to Embodiment 2, there is utilized a configuration in which the respective shapes of the foundation portion 25 and the detachable portion 26 of the shielding material 12 differ from each other in the beam axis direction, i.e., no engagement portion that accounts for the half or more of the shielding material 12 exists in the axis direction, the detachable portion can be made detachable while sufficiently ensuring the secondary-radiation attenuation effect even in the engagement portion where the detachable portion 26 and the foundation portion 25 engage with each other.

Because the rotating gantry 10 according to Embodiment 2 includes the shielding material 12 at the downstream side of the irradiation subject 13, a secondary radiation can be prevented from leaking out of the rotating gantry 10. The shielding material 12 is configured with the foundation portion 25 and the detachable portion 26; thus, without providing the shielding material moving apparatus 19, the isocenter IC and the floor reference mark 23 on the building floor 22 can optically be ascertained by removing the detachable portion 26 when the maintenance is implemented.

In the case of a facility where the detachable portion 26 is frequently detached and attached, the material of the detachable portion 26 may differ from that of the foundation portion 25; for example, only the detachable portion 26 may be formed of aluminum that is hardly activated by a secondary radiation. As an example in which the material of the detachable portion 26 differs from that of the foundation portion 25, the foundation portion 25 may be formed of ordinary concrete and the detachable portion 26 may be formed of heavy concrete so that the shielding capacity of the detachable portion 26 is reinforced.

Embodiment 3

Figure 12:
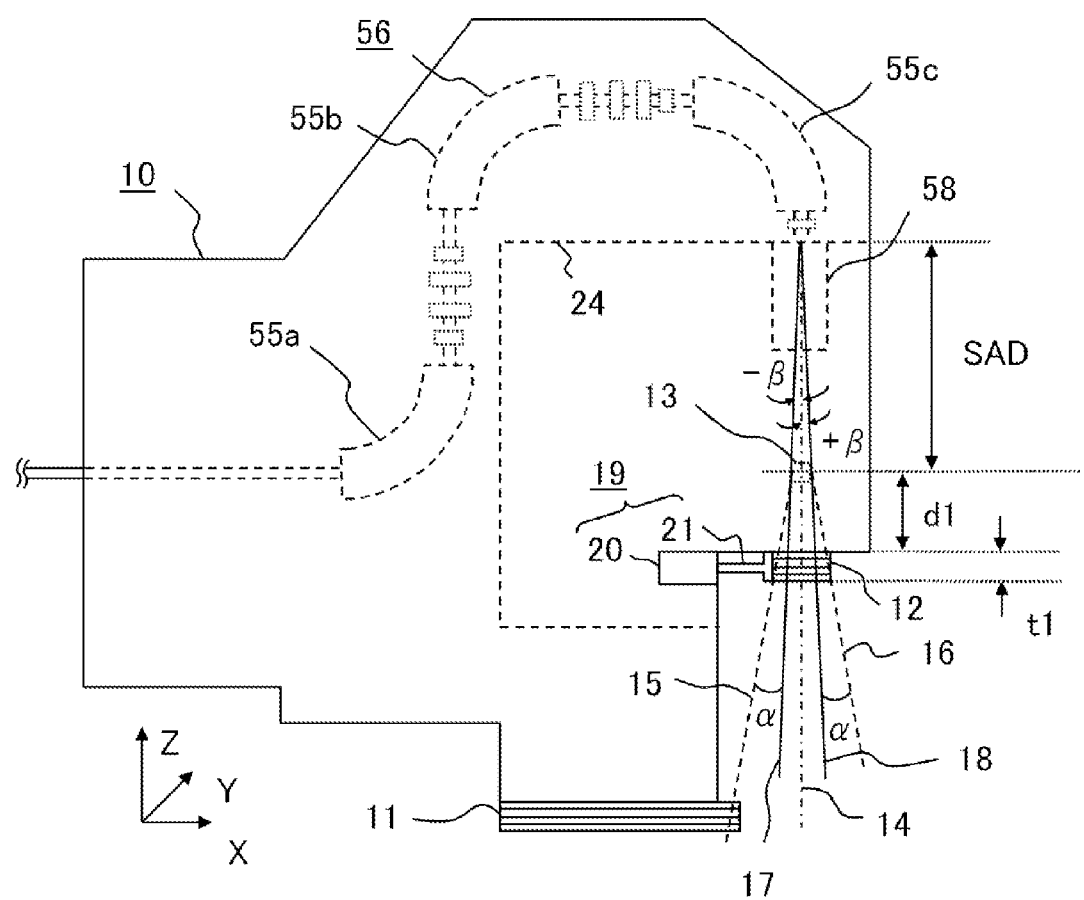
FIG. 12 is a diagram representing the configuration of a rotating gantry according to Embodiment 3 of the present invention.

FIG. 12 is a diagram representing the configuration of a rotating gantry according to Embodiment 3 of the present invention. The rotating gantry 10 according to Embodiment 3 differs from those according to Embodiments 1 and 2 in that the counter weight 11 has part of the function of the shielding material 12, i.e., the counter weight 11 plays part of the role of the shielding material. Specifically, the counter weight 11 is extended toward the beam center line 14 so that a secondary radiation having the angle α passes through the counter weight 11.

The rotating gantry 10 according to Embodiment 3 has the shielding material 12 at the downstream side of the irradiation subject 13, and the counter weight 11 attenuates the leakage dose of a secondary radiation; therefore, a secondary radiation can be prevented from leaking out of the rotating gantry 10. In the rotating gantry 10 according to Embodiment 3, when passing through the counter weight 11, part of secondary radiations are attenuated; therefore, the shielding material 12 can be made smaller than that of the rotating gantry 10 according to each of Embodiments 1 and 2.

Embodiment 4

Figure 13:
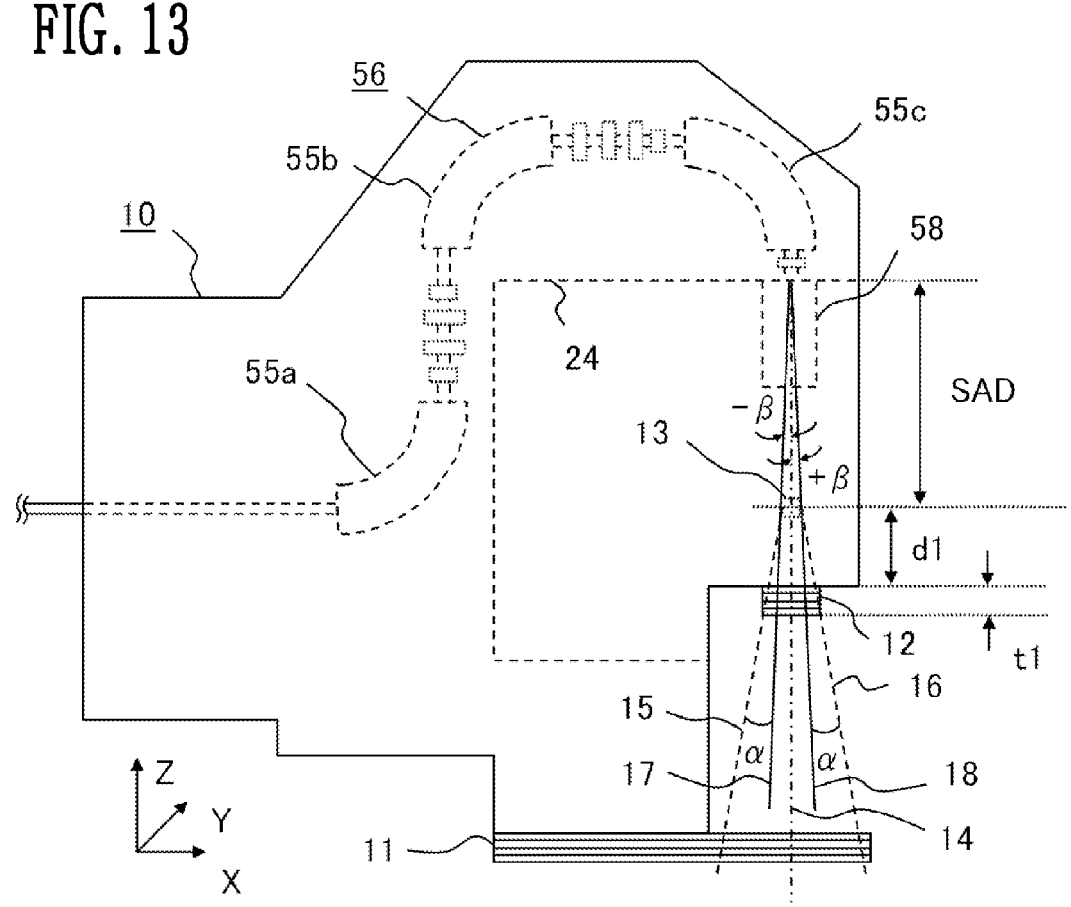
FIG. 13 is a diagram representing the configuration of a rotating gantry according to Embodiment 4 of the present invention.

FIG. 13 is a diagram representing the configuration of a rotating gantry according to Embodiment 4 of the present invention. The rotating gantry 10 according to Embodiment 4 differs from that according to Embodiments 3 in that the counter weight 11 is extended beyond the beam axis so that all the secondary radiations within the angle α can pass through the counter weight 11.

The rotating gantry 10 according to Embodiment 4 includes the shielding material 12 at the downstream side of the irradiation subject 13, and the counter weight 11 attenuates the leakage dose of a secondary radiation within the angle α; therefore, a secondary radiation can be prevented from leaking out of the rotating gantry 10. When passing through the counter weight 11, all the secondary radiations within the angle α are further attenuated; therefore, the rotating gantry 10 according to Embodiment 4 can raise the effect of preventing a secondary radiation from leaking, in comparison with the rotating gantry 10 according to each of Embodiments 1 through 3.

Figure 14:
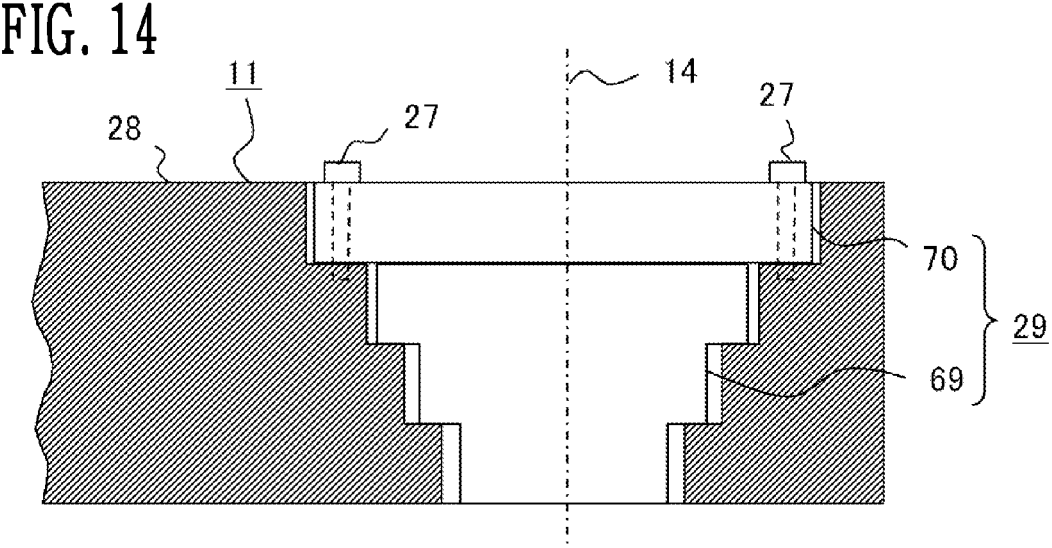
FIG. 14 is a diagram representing a counter weight including a detachable portion.

The portion, around the beam center line 14, of the counter weight 11 may be made detachable. FIG. 14 is a diagram representing a counter weight including a detachable portion. An example is represented in which the counter weight 11 has a detachable portion 29 including a first detachable portion 69 and a second detachable portion 70. In FIG. 14, the main body of the counter weight 11 is represented by a cross section so that the detachable portion 29 is exposed. The bolt 27 connects the main body 28 with the second detachable portion 70 of the detachable portion 29. FIG. 14 shows an example in which the main body 28 and the detachable portion 29 each have a 4-iron-plate laminated structure and stepped engagement portions; an example is represented in which there is provided engagement portions where the detachable portion 29, which is detachable, engage with the main body 28. The first detachable portion 69 includes three iron plates, and the second detachable portion 70 includes one iron plate. After the first detachable portion 69 is inserted into the main body 28, the second detachable portion mounted in such a way as to cover the first detachable portion 69. FIG. 14 shows an example in which as is the case with the engagement portion of the shielding material 12 explained in Embodiment 2, the engagement portion where the detachable portion 29, which is attachable and detachable, engages with the main body 28 includes a portion that is parallel to the beam axis (the axis that passes through the beam center line 14) of the charged particle beam 31 and a portion that is perpendicular to the beam axis. When the positional relationship between the rotating gantry 10 and the building is ascertained or the position adjustment is implemented, the detachable portion 29 of the counter weight 11 and the detachable portion 26 of the shielding material 12 are detached, so that the isocenter IC and the floor reference mark 23 on the building floor 22 can optically be ascertained.

In the case of a facility where the detachable portion 29 is frequently detached and attached, the material of the detachable portion 29 may differ from that of the main body 28; for example, only the detachable portion 29 may be formed of aluminum that is hardly activated by a secondary radiation. As an example in which the material of the detachable portion 29 differs from that of the main body 28, the main body 28 may be formed of ordinary concrete and the detachable portion 29 may be formed of heavy concrete so that the shielding capacity of the detachable portion 29 is reinforced.

When in the counter weight 11 according to Embodiment 4, there is utilized a configuration in which the respective shapes of the main body 28 and the detachable portion 29 of the counter weight 11 differ from each other in the beam axis direction, i.e., no engagement portion that accounts for the half or more of the counter weight 11 having a function as a leakage dose shielding material exists in the axis direction, the detachable portion 29 can be made detachable while sufficiently ensuring the secondary-radiation attenuation effect even in the engagement portion where the detachable portion 29 and the main body 28 engage with each other.

In the case where the detachable portion 29 is not provided in the counter weight 11, an arm or the like is provided from the floor reference mark 23 on the building floor 22 to the beam center line 14, avoiding the counter weight 11, and a reference mark is provided on a point at which the beam center line 14 passes through the arm, so that the isocenter IC and the reference mark based on the floor reference mark 23 on the building floor 22 can optically be ascertained. It may also be allowed that a sliding mechanism is provided in the counter weight 11 and is slid so that the counter weight 11 does not intersect the beam center line 14 when the positional relationship between the rotating gantry 10 and the building is ascertained or the position adjustment is implemented.

Embodiment 5

Figure 15:
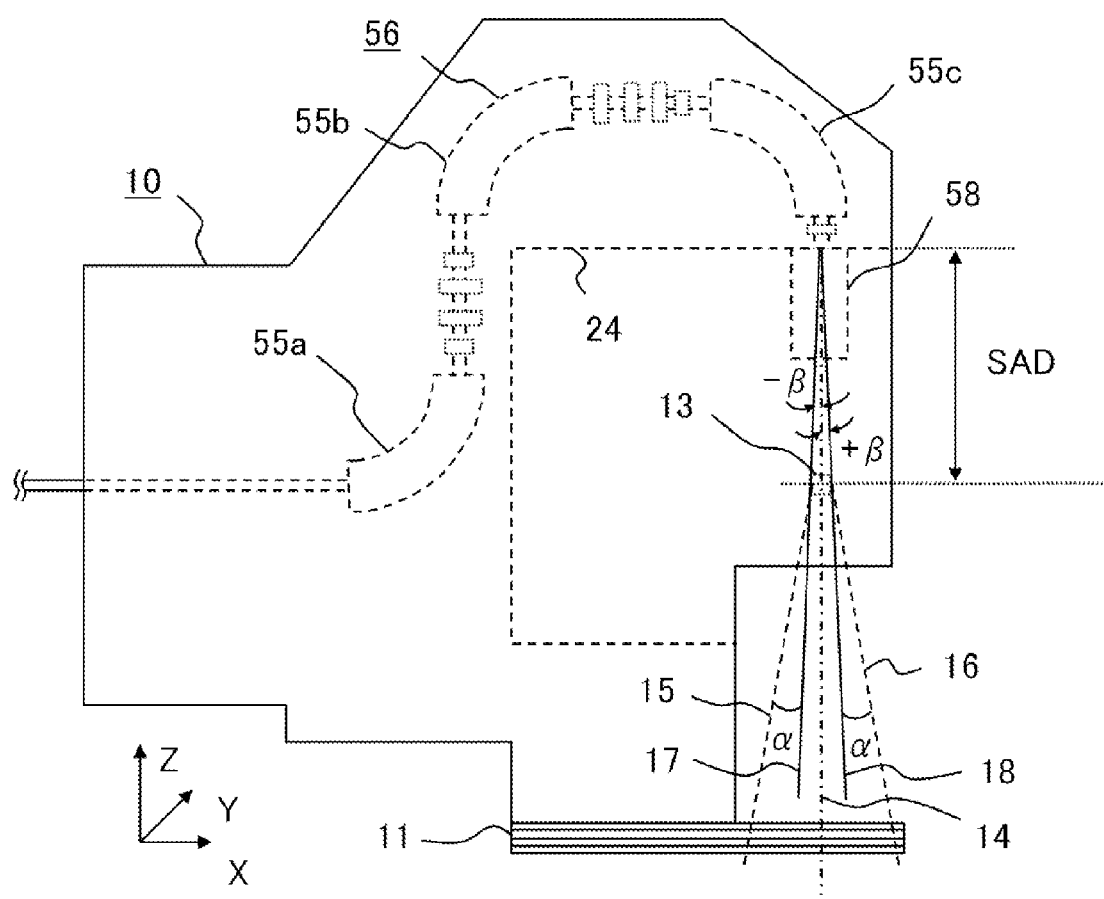
FIG. 15 is a diagram representing the configuration of a rotating gantry according to Embodiment 5 of the present invention.

FIG. 15 is a diagram representing the configuration of a rotating gantry according to Embodiment 5 of the present invention. The rotating gantry 10 according to Embodiment 5 differs from the rotating gantry 10 according to each of Embodiments 1 through 4 in that the shielding material 12 is not provided therein and the counter weight 11 is extended beyond the beam axis so that all the secondary radiations within the angle α can pass through the counter weight 11.

The rotating gantry 10 according to Embodiment 5 includes the counter weight 11 at the downstream side of the irradiation subject 13, and the counter weight 11 attenuates the leakage dose of a secondary radiation within the angle α; therefore, a secondary radiation can be prevented from leaking out of the rotating gantry 10. Because in the rotating gantry 10 according to Embodiment 5, the counter weight 11 functions also as a shielding material for a secondary radiation, it is not required an extra shielding material and hence there is demonstrated an advantage that the structure thereof can be simplified.

As explained in Embodiment 4, the portion, around the beam center line 14, of the counter weight 11 may be made detachable. When the positional relationship between the rotating gantry 10 and the building is ascertained or the position adjustment is implemented, the detachable portion 29 of the counter weight 11 is detached, so that the isocenter IC and the floor reference mark 23 on the building floor 22 can optically be ascertained. In the case where the detachable portion 29 is not provided in the counter weight 11, it may be allowed that an arm or the like is provided from the floor reference mark 23 on the building floor 22 to the beam center line 14, avoiding the counter weight 11, and a reference mark is provided on a point at which the beam center line 14 passes through the arm. It may also be allowed that a sliding mechanism is provided in the counter weight 11 and is slid so that the counter weight 11 does not intersect the beam center line 14 when the positional relationship between the rotating gantry 10 and the building is ascertained or the position adjustment is implemented. When the positional relationship between the rotating gantry 10 and the building is ascertained or the position adjustment is implemented, the isocenter IC and the reference mark based on the floor reference mark 23 on the building floor 22 are optically ascertained.

Embodiment 6

Figure 16A:
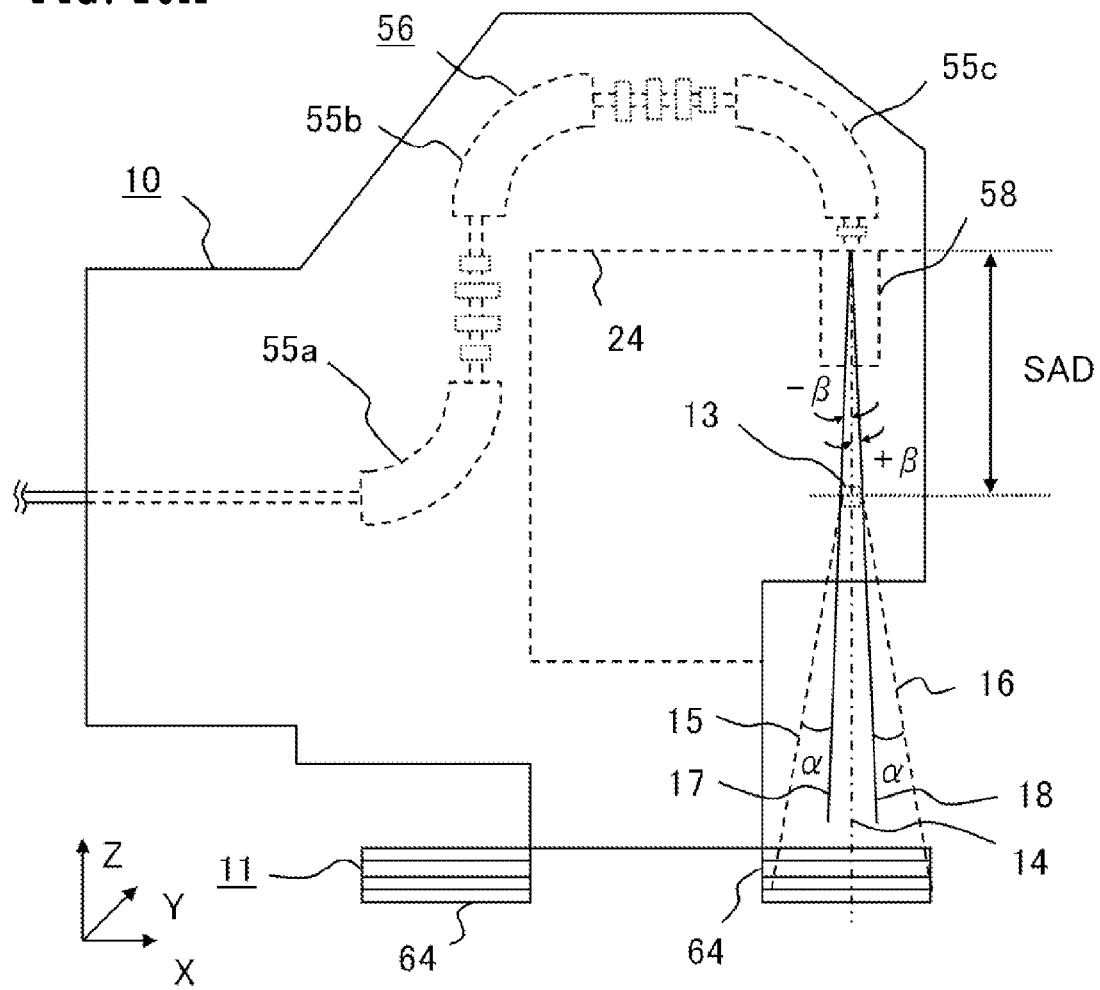
FIG. 16A and FIG. 16B are diagrams representing the configuration of a rotating gantry and a small weight portion according to Embodiment 6 of the present invention.
Figure 16B:
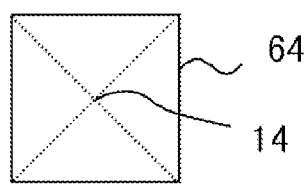

FIG. 16A and FIG. 16B are diagrams representing the configuration of a rotating gantry and a small weight portion according to Embodiment 6 of the present invention. FIG. 16A is a diagram representing the configuration of a rotating gantry according to Embodiment 6 of the present invention; FIG. 16B is a top view of a small weight portion when viewed from the rotating gantry mounting portion. The rotating gantry 10 according to Embodiment 6 differs from the rotating gantry 10 according to Embodiment 5 in that the counter weight 11 is divided into a plurality of counter weights. FIG. 16 represents an example in which the counter weight 11 is formed of two small weight portions 64 and the small weight portion 64 is a rectangular parallelepiped. In FIG. 16B, the beam center line intersects the small weight portion 64 at the intersection point of the diagonal lines, in the quadrangle representing the outline of the small weight portion 64, that are each indicated by a broken line.

It is desirable that the thickness of the counter weight 11, which is situated, as a shielding material for attenuating the leakage dose of a secondary radiation, at the downstream side of the irradiation subject 13, is increased. When the counter weight 11 is provided divided in such a way the thickness of the counter weight 11 through which the beam center line 14 passes is increased, so that the effect of attenuating the leakage dose of a secondary radiation can be enhanced.

The rotating gantry 10 according to Embodiment 6 includes the small weight portion 64 of the counter weight 11 at the downstream side of the irradiation subject 13, and the small weight portion 64 attenuates the leakage dose of a secondary radiation within the angle α; therefore, a secondary radiation can be prevented from leaking out of the rotating gantry 10. Because the counter weight 11 is configured with a plurality of small weight portions 64, it is possible to make the thickness of the small weight portion 64 larger than the thickness of the counter weight 11 according to Embodiment 5, which is a single and undivided member; thus, the effect of attenuating the leakage dose of a secondary radiation can be enhanced.

Embodiment 7

Figure 17A:
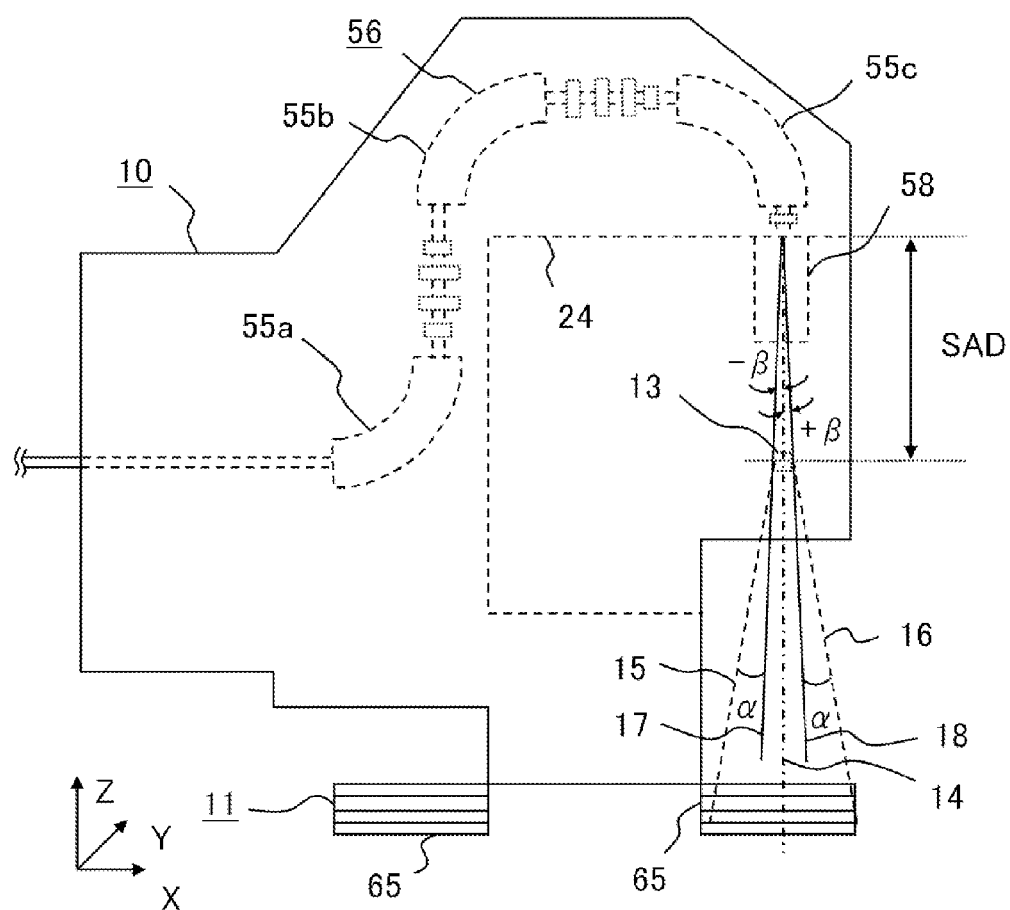
FIG. 17A and FIG. 17B are diagrams representing the configuration of a rotating gantry and a small weight portion according to Embodiment 7 of the present invention.
Figure 17B:
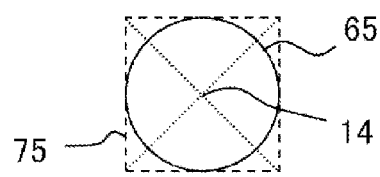

FIG. 17 A and FIG. 17B are diagrams representing the configuration of a rotating gantry and a small weight portion according to Embodiment 7 of the present invention. FIG. 17A is a diagram representing the configuration of a rotating gantry according to Embodiment 7 of the present invention; FIG. 17B is a top view of a small weight portion when viewed from the rotating gantry mounting portion. The rotating gantry 10 according to Embodiment 7 differs from the rotating gantry 10 according to Embodiment 6 in that the shape of the small weight portion thereof is different from that of the small weight portion according to Embodiment 6. FIG. 17 represents an example in which the counter weight 11 is formed of two small weight portions 65 and the small weight portion 65 is a cylindrical object that is concentric with the beam axis. In FIG. 17B, the beam center line 14 passes through the center of the cylindrical object, i.e., the beam center line 14 intersects the cylindrical object (small weight portion 65) at the intersection point of the diagonal lines of the circumscribed quadrangle 75 represented by a broken line that is circumscribed around the cylindrical object (small weight portion 65).

When as represented in FIG. 17, the small weight portion 65 of the counter weight 11 is disposed in such a way as to be concentric with the beam axis, the secondary-radiation attenuation effect per counter-weight unit weight is raised. For example, in a therapy apparatus having a circular irradiation field (i.e., enlarged irradiation or broad irradiation), the small weight portion whose beam-direction cross section is circular can be downsized up to approximately ¾ of the small weight portion whose beam-direction cross section is square (e.g., the circumscribed quadrangle 75).

The rotating gantry 10 according to Embodiment 7 includes the small weight portion 65 of the counter weight 11 at the downstream side of the irradiation subject 13, and the small weight portion 65 attenuates the leakage dose of a secondary radiation within the angle α; therefore, a secondary radiation can be prevented from leaking out of the rotating gantry 10. Because the small weight portion 65 of the counter weight 11 is a cylindrical object and the center axis (the center axis of the cylindrical object) of the small weight portion 65 situated at the downstream side of the irradiation subject 13 coincide with the beam axis, the effect of attenuating the leakage dose of a secondary radiation per counter-weight unit weight is raised in comparison with the rotating gantry 10 according to Embodiment 6.

Embodiment 8

Figure 18:
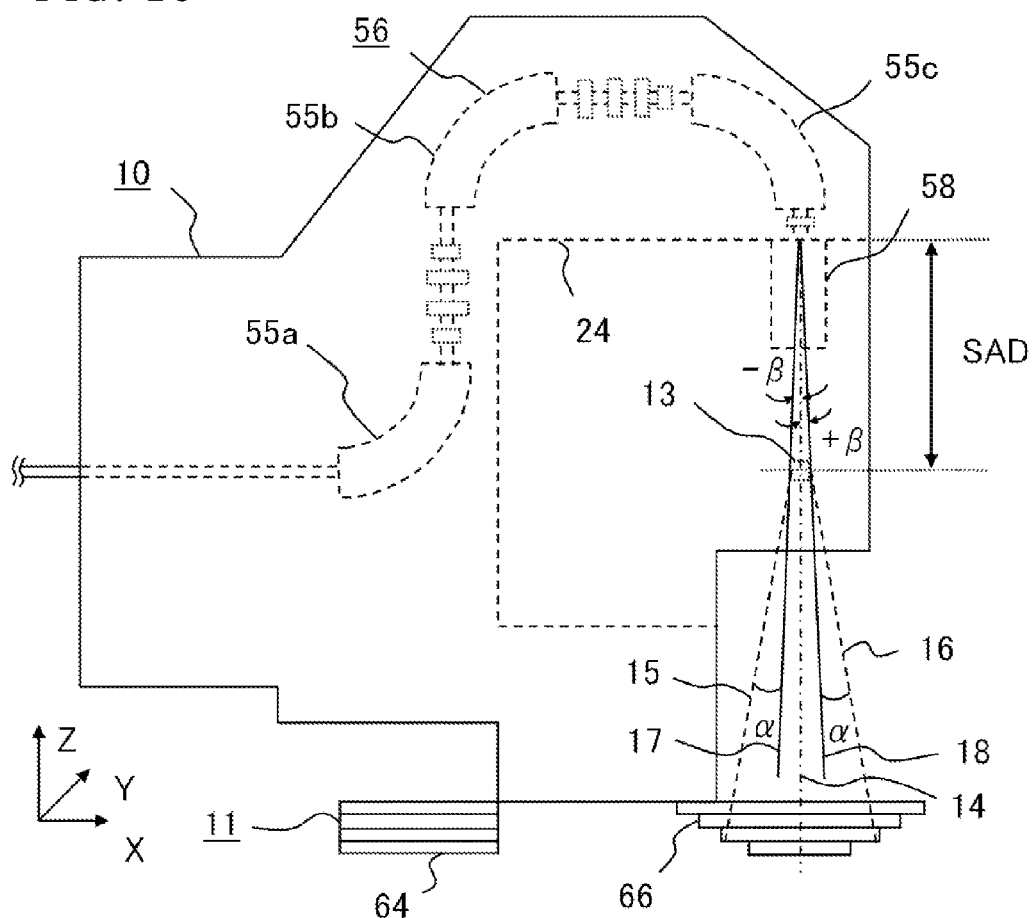
FIG. 18 is a diagram representing the configuration of a rotating gantry according to Embodiment 8 of the present invention.

FIG. 18 is a diagram representing the configuration of a rotating gantry according to Embodiment 8 of the present invention. The rotating gantry 10 according to Embodiment 8 differs from those according to Embodiments 6 and 7 in that a small weight portion 66 of the counter weight 11 situated at the downstream side of the irradiation subject 13 has a special shape. FIG. 18 represents an example in which the small weight portion 66 of the counter weight 11, situated at the downstream side of the irradiation subject 13, has a shape, where the area that is perpendicular to the beam center line 14 decreases stepwise as the small weight portion 66 recedes from the isocenter IC. And FIG. 18 represents an example in which another small weight portion is the small weight portion 64, which is a rectangular parallelepiped. The shape of the small weight portion 64 is not limited to a rectangular parallelepiped; it may be another shape.

With a high probability, a secondary radiation is emitted forward in the beam direction, and the energy and the transmittance of a radiation that is emitted forward in the beam direction are high. The small weight portion 66 is thick in the beam axis direction and is thin in the directions shifted from the beam center line 14, so that the small weight portion whose weight is the same as the weight of another type small weight portion can efficiently be utilized as a shielding material.

The rotating gantry 10 according to Embodiment 8 includes the small weight portion 66 of the counter weight 11 situated at the downstream side of the irradiation subject 13 and the small weight portion 66 whose area that is perpendicular to the beam center line 14 decreases stepwise as the small weight portion 66 recedes from the isocenter IC attenuates the leakage dose of a secondary radiation within the angle α; therefore, a secondary radiation can be prevented from leaking out of the rotating gantry 10. The area, of the small weight portion 66 of the counter weight 11, that is perpendicular to the beam center line decreases stepwise as the small weight portion 66 recedes from the isocenter; therefore, the rotating gantry 10 according to Embodiment 8 can efficiently be utilized as a shielding material, in comparison with the rotating gantry 10 according to each of Embodiments 6 and 7.

As the irradiation method for the particle beam irradiation apparatus 58, a scanning irradiation method has been explained; however, the present invention can be applied to a broad irradiation method in which the charged particle beam 31 is enlarged in a dispersion manner by a scatterer, and the shape of the enlarged charged particle beam 31 is made to coincide with the shape of the irradiation subject 13 in order to form an irradiation field. The present invention can be applied to any one of other scanning irradiation methods than the scanning irradiation method explained in Embodiment 1, i.e., the spot scanning method, the raster scanning method, and the like. In the scope of the present invention, the embodiments thereof can freely be combined with one another and can appropriately be modified or omitted.

DESCRIPTION OF REFERENCE NUMERALS

10: rotating gantry
11: counter weight
12: shielding material
13: irradiation subject
19: shielding material moving apparatus
25: foundation portion
26: detachable portion
28: main body
29: detachable portion
31: charged particle beam
51: particle beam therapy system
52: beam generation apparatus
54: synchrotron (accelerator)
56: rotating gantry mounting portion 58, 58a, 58b: particle beam irradiation apparatus
59: beam transport system
64, 65, 66: small weight portion

The invention claimed is:

1. A rotating gantry that is equipped with a particle beam irradiation apparatus that irradiates a charged particle beam onto an irradiation subject and that can rotate around an isocenter,
    wherein a shielding material that attenuates a leakage dose of a secondary radiation generated by collision of the charged particle beam with the irradiation subject is provided at a position that is situated at the side opposed to the particle beam irradiation apparatus with respect to the irradiation subject and through which a beam axis of the charged particle beam is obstructed during irradiation, said beam axis being an axis that passes through a center line of the charged particle beam, and
    wherein the shielding material is disposed in such a way that when the irradiation subject does not exist in the rotating gantry, a portion of the shielding material that intersects the beam axis of the charged particle beam, is attachable and detachable, or can move in a sliding manner and in the rotation-axle direction of the rotating gantry to prevent obstruction, by the shielding material, of the beam axis and to enable ascertainment of the isocenter and a floor reference mark.

2. The rotating gantry according to claim 1, wherein there is provided a shielding material moving apparatus that moves the shielding material in the sliding manner and in the rotation-axle direction of the rotating gantry in such a way that the shielding material intersects the beam axis of the charged particle beam or departs from the beam axis.

3. The rotating gantry according to claim 1,
    wherein the shielding material includes a foundation portion fixed with respect to the beam axis of the charged particle beam and a detachable portion that is the beam axis portion and that is attachable and detachable, and
    wherein the shielding material is disposed in such a way that the detachable portion thereof intersects the beam axis of the charged particle beam.

4. The rotating gantry according to claim 3, wherein the shielding material includes a step-like engagement portion where the foundation portion and the detachable portion engage with each other.

5. The rotating gantry according to claim 3,
    wherein the shielding material includes an engagement portion where the foundation portion and the detachable portion engage with each other, and
    wherein when the engagement portion includes a beam axis parallel engagement portion where the foundation portion and the detachable portion engage with each other in a direction parallel to the beam axis, no portion of the beam axis parallel engagement portion defines a length that accounts for at least half of the length of the shielding material in the direction parallel to the beam axis.

6. The rotating gantry according to claim 3, wherein the material of the detachable portion is different from that of the foundation portion.

7. A particle beam therapy system comprising:
    a beam generation apparatus that generates a charged particle beam and accelerates the charged particle beam by means of an accelerator;
    a beam transport system that transports the charged particle beam accelerated by the accelerator;
    a particle beam irradiation apparatus that irradiates the charged particle beam transported by the beam transport system onto an irradiation subject; and
    a rotating gantry that is equipped with the particle beam irradiation apparatus and can rotate around the isocenter, wherein the rotating gantry is according to claim 1.

* * * * *